United States Patent
Jonckheere et al.

(10) Patent No.: US 11,160,684 B2
(45) Date of Patent: Nov. 2, 2021

(54) AUTOSTABLE BICANALICULAR PROBE

(71) Applicant: FRANCE CHIRURGIE INSTRUMENTATION SAS, Paris (FR)

(72) Inventors: Paul Jonckheere, Antwerp (BE); Abraham Ferron, Bordeaux (FR)

(73) Assignee: FRANCE CHIRURGIE INSTRUMENTATION SAS, Paris (FR)

( * ) Notice: Subject to any disclaimer, the term of this patent is extended or adjusted under 35 U.S.C. 154(b) by 250 days.

(21) Appl. No.: 16/044,667

(22) Filed: Jul. 25, 2018

(65) Prior Publication Data
US 2019/0029884 A1 Jan. 31, 2019

(30) Foreign Application Priority Data
Jul. 25, 2017 (FR) ..................................... 17 70792

(51) Int. Cl.
| A61F 9/00 | (2006.01) |
| A61F 9/007 | (2006.01) |
| A61B 17/12 | (2006.01) |

(52) U.S. Cl.
CPC .... *A61F 9/00772* (2013.01); *A61B 17/12022* (2013.01)

(58) Field of Classification Search
CPC .............. A61F 9/00772; A61F 9/007; A61B 17/12022; A61M 29/02; A61M 25/10; A61M 2025/1054
See application file for complete search history.

(56) References Cited

U.S. PATENT DOCUMENTS

| 3,948,272 A | * | 4/1976 | Guibor | A61F 9/00772 604/264 |
| 5,437,625 A | * | 8/1995 | Kurihashi | A61F 9/00772 128/898 |
| 6,117,116 A | * | 9/2000 | Walsh | A61F 9/00772 604/264 |
| 6,547,765 B1 | * | 4/2003 | Walsh | A61F 9/00772 604/264 |
| 2007/0255263 A1 | | 11/2007 | Sugimoto | |
| 2012/0158035 A1 | * | 6/2012 | Schaeffer | A61M 25/104 606/194 |
| 2014/0364790 A1 | | 12/2014 | Matsumoto et al. | |

FOREIGN PATENT DOCUMENTS

| FR | 2 741 538 A1 | 5/1997 | |
| FR | 2741538 A1 | * 5/1997 | ......... A61F 9/00772 |

OTHER PUBLICATIONS

French Search Report (Application No. 1770792) (2 pages—dated Mar. 12, 2018).

* cited by examiner

*Primary Examiner* — Nathan R Price
*Assistant Examiner* — Courtney B Fredrickson
(74) *Attorney, Agent, or Firm* — Renner Kenner Greive Bobak Taylor and Weber; Tama L. Drenski

(57) ABSTRACT

A bicanalicular probe intended to be inserted into the nasolacrimal duct of a patient including a central tubular part 1 made from a material compatible with insertion into the human body, preferably silicone, and two termination parts 4, 5 each fixed to one end of the central tubular part 1, characterized in that the two thickened parts 6, 7 project from the central tubular part, the two thickened parts being firstly at a distance from each other and secondly each at a distance from the ends 2, 3 where the termination parts are attached.

15 Claims, 1 Drawing Sheet

AUTOSTABLE BICANALICULAR PROBE

TECHNICAL FIELD

The present invention relates to a bicanalicular probe intended to be inserted into the nasolacrimal duct of a patient.

BACKGROUND ART

Classically, a bicanalicular probe intended to be inserted into the nasolacrimal duct of a patient comprises a central tube forming a probe made from a material compatible with insertion into the human body, notably silicone, that is connected at its opposite ends to termination parts, for example guide wires, mandrels or the like, that permit the introduction of the central silicone tube into the nasolacrimal duct.

These early devices, although constituting a particularly appropriate solution for insertion into the nasolacrimal duct, are difficult for the surgeon to manipulate to obtain the correct position in the nasolacrimal duct and require the strands of the central tube to be tied after fitting. U.S. Pat. No. 6,117,116, describes a probe according to the preamble of claim 1. A tube is formed at the interface between the central tube and the respective termination parts.

SUMMARY OF THE INVENTION

The present invention aims to overcome the difficulties of early devices by proposing a bicanalicular probe intended to be inserted into the nasolacrimal duct of a patient, as defined in claim 1.

For preference, the two thickened parts are produced in the form of two tubes fixed around the central tubular part.

For preference, the two thickened parts, that is the two tubes, are at the same distance from the end where the termination part on the opposite side to the other thickened part is attached, that is the tube.

For preference, the two thickened parts, that is the two tubes, extend along the tube for a length of between 4 mm and 8 mm, preferably between 5 mm and 7 mm.

For preference, the distance along the tube between the two thickened parts, that is the two tubes, represents a central segment of length between 30 mm and 40 mm, preferably between 32 mm and 35 mm.

According to a preferred method of implementation of the invention, the two tubes are bonded to the central tubular part.

According to a preferred method of implementation of the invention, the two terminations consist of guide wires, each guide wire being connected to the tube without any roughness causing it to project laterally that could catch "during insertion".

According to another method of implementation, a metal mandrel could be provided, preferably with an external diameter of 0.4 mm and a length of 60 mm, bonded to the inside of the silicone tube.

According to an improvement, a mark is provided half way between the two tubes to assist in positioning by the surgeon.

Providing such a bicanalicular probe according to the invention, the surgeon can ensure that when fitting the probe, the two tubes are placed in the lacrimal sac and not in the horizontal part of the canalicules or in the nasolacrimal duct. The probe is therefore more mobile and free in position in the duct creating less traction on the meati and avoiding "Cheese wiring" phenomena. Furthermore, it is no longer necessary to tie the silicone strands after fitting, withdrawal being effected by pulling on the central segment, and it is no longer necessary to cut the knot in the nose.

The stability of the probe is particularly good, due to the presence of two tubes in the sac. Finally, the central mark assists in positioning the probe when fitting by pulling on the strands of the terminations in such a way that the tubes are precisely located in the sac.

BRIEF DESCRIPTION OF THE DRAWINGS

As an example, a preferred method of implementation of the invention will now be described by referring to the drawings, wherein.

PREFERRED EMBODIMENT FOR CARRYING OUT THE INVENTION

Figure 1:
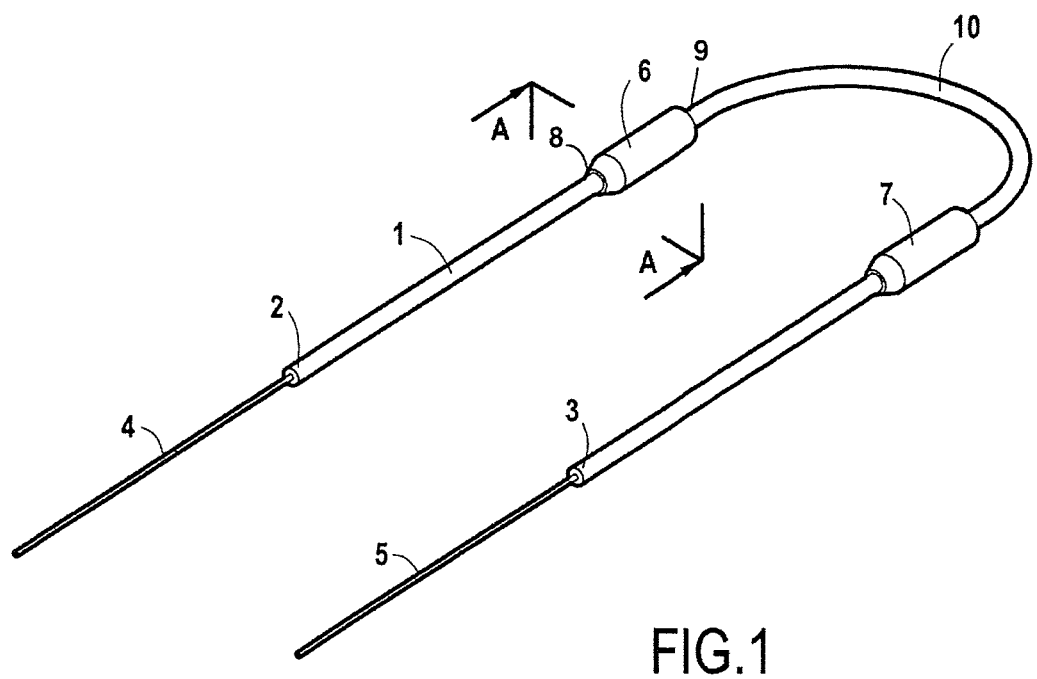
FIG. 1 is a schematic view of a bicanalicular probe according to the invention.
Figure 2:
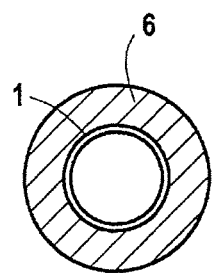
FIG. 2 is a cross sectional view along the line A-A in FIG. 1.

FIG. 1 shows a bicanalicular probe intended to be inserted into the nasolacrimal duct of a patient. This probe consists of a silicone tube 1 that extends between two end points 2 and 3. Two termination parts 4 and 5 protrude from the end points 2 and 3 and enable the probe to be inserted. The parts 4 and 5 are thinner than the tube 1.

These termination parts can be guide wires, preferably in PEEK, as described in patent FR-A-2992851 and in which the tube/guide wire joint is chamfered to prevent any roughness from rubbing against the nasal wall during insertion.

The parts 4 and 5 may also be mandrels as shown in the document U.S. Pat. No. 4,380,239 in which the tube/mandrel joint is also chamfered. They may also be mandrels, preferably of external diameter 0.80 mm and length 80 mm, assembled with the silicone tube 1 as described in patent FR-A-2700722. They may also be metal mandrels of external diameter 0.4 mm and length 60 mm bonded to the inside of the silicone tube.

The silicone tube 1 has a diameter of 0.3 mm to 0.64 mm, the total length of the silicone tube, excluding the terminations, being for example 300 mm.

Two tubes 6 and 7 forming the thickened parts of the tube project laterally from the silicone tube 1. They should preferably be fixed to the tube by bonding, welding or similar. They can also be produced by moulding or overmoulding. The two tubes 6 and 7 extend for a length along the tube 1 of between 4 mm and 8 mm, preferably between 5 mm and 7 mm. Between the two tubes 6 and 7, a central segment of the silicone tube 1 is specified which has a length measured along the tube of between 30 mm and 40 mm, preferably between 32 mm and 35 mm. At the median point, that is half way between the two tubes 6 and 7, a central mark 10 is formed defining the exact midpoint enabling the surgeon to fit it more easily, in particular by ensuring that the two tubes 6 and 7 are correctly located in the lacrimal sac.

The central mark 10 may consist of a thinner portion of the central tube 1. It may also consist of a marking, preferably by pad printing with a biocompatible coloured ink in the form of a point on the surface of the tube, a continuous or discontinuous line of 360° or less on the surface around the tube, a portion of the central tube filled with ink or silicone adhesive (a transparent material), or any other form of mark or similar marking.

The two tubes or thickened parts extend between the two respective distal and proximal end points 8, 9 of the tube 1.

The two proximal points 9 are at a distance from each other.

Each distal point 8 is at a distance from points 2, 3 of the respective tube which is located on the opposite side to the respective proximal points 9 from which the respective parts 4, 5 extend.

What is claimed is:

1. A bicanalicular probe intended to be inserted into the nasolacrimal duct of a patient, comprising a central tubular part (1) made from a material compatible with insertion into the human body and two termination parts (4, 5) each fixed to the central tubular part so that they project from two respective distal ends (2, 3) of the central tubular part, characterized in that said central tubular part comprises two thickened parts (6, 7) each extending between two respective distal and proximal thickened part end points and being at a distance from one another so as to form projections, said respective distal thickened part end points each being at a distance from the respective distal ends (2, 3) of the central tubular part, and wherein the two distal thickened part end points are disposed on said central tubular part, wherein the two thickened parts (6, 7) are bonded to the central tubular part by a layer of adhesive.

2. The probe according to claim 1, characterized in that the two thickened parts (6, 7) are in the form of two tubes fixed around the central tubular part.

3. The probe according to claim 2, characterized in that the distance along the central tubular part between the proximal end points of the two thickened parts (6, 7) in the form of two tubes corresponds to a central segment of length between 30 mm and 40 mm.

4. The probe according to claim 1, characterized in that the two thickened parts extend along the central tubular part for a length of between 4 mm and 8 mm.

5. The probe according to claim 1, characterized in that the two respective distal end points of the thickened parts are at the same respective distance from the distal ends (2, 3) of the central tubular part on the side opposite to the other thickened part.

6. A bicanalicular probe intended to be inserted into the nasolacrimal duct of a patient, comprising a central tubular part (1) made from a material compatible with insertion into the human body and two termination parts (4, 5) each fixed to the central tubular part so that they project from two respective distal ends (2, 3) of the central tubular part, characterized in that said central tubular part comprises two thickened parts (6, 7) each extending between two respective distal and proximal thickened part end points and being at a distance from one another so as to form projections, said respective distal thickened part end points each being at a distance from the respective distal ends (2, 3) of the central tubular part, and wherein the two distal thickened part end points are disposed on said central tubular part, wherein the two thickened parts (6, 7) are welded to the central tubular part.

7. The probe according to claim 6, characterized in that the two thickened parts (6, 7) are in the form of two tubes fixed around the central tubular part.

8. The probe according to claim 7, characterized in that the distance along the central tubular part between the proximal end points of the two thickened parts (6, 7) in the form of two tubes corresponds to a central segment of length between 30 mm and 40 mm.

9. The probe according to claim 6, characterized in that the two thickened parts extend along the central tubular part for a length of between 4 mm and 8 mm.

10. The probe according to claim 6, characterized in that the two respective distal end points of the thickened parts are at the same respective distance from the distal ends (2, 3) of the central tubular part on the side opposite to the other thickened part.

11. A bicanalicular probe intended to be inserted into the nasolacrimal duct of a patient, comprising a central tubular part (1) made from a material compatible with insertion into the human body and two termination parts (4, 5) each fixed to the central tubular part so that they project from two respective distal ends (2, 3) of the central tubular part, characterized in that said central tubular part comprises two thickened parts (6, 7) each extending between two respective distal and proximal thickened part end points and being at a distance from one another so as to form projections, said respective distal thickened part end points each being at a distance from the respective distal ends (2, 3) of the central tubular part, and wherein the two distal thickened part end points are disposed on said central tubular part, wherein the two thickened parts (6, 7) are molded or over-molded to the central tubular part.

12. The probe according to claim 11, characterized in that the two thickened parts (6, 7) are in the form of two tubes fixed around the central tubular part.

13. The probe according to claim 12, characterized in that the distance along the central tubular part between the proximal end points of the two thickened parts (6, 7) in the form of two tubes corresponds to a central segment of length between 30 mm and 40 mm.

14. The probe according to claim 11, characterized in that the two thickened parts extend along the central tubular part for a length of between 4 mm and 8 mm.

15. The probe according to claim 11, characterized in that the two respective distal end points of the thickened parts are at the same respective distance from the distal ends (2, 3) of the central tubular part on the side opposite to the other thickened part.

* * * * *